United States Patent [19]

Shimoni et al.

[11] Patent Number: 4,692,864

[45] Date of Patent: Sep. 8, 1987

[54] METHOD OF DETERMINING STENOSIS OF BLOOD VESSELS

[75] Inventors: Yair Shimoni, Jerusalem; Paul Fenster, Petach Tikva; Bilha Nissenson, Herzlia, all of Israel

[73] Assignee: Elscint Ltd., Haifa, Israel

[21] Appl. No.: 737,144

[22] Filed: May 23, 1985

[51] Int. Cl.$^4$ .................. G01N 23/00; A61B 5/02
[52] U.S. Cl. .................. 364/414; 128/661; 378/99
[58] Field of Search .................. 364/414, 415, 416; 128/661, 663, 659, 653, 654; 358/111; 378/99

[56] References Cited

U.S. PATENT DOCUMENTS

| | | |
|---|---|---|
| 4,111,191 | 9/1978 | Sherro .................. 128/659 |
| 4,154,231 | 5/1979 | Russel .................. 128/663 |
| 4,326,252 | 4/1982 | Kohno et al. .................. 364/414 |
| 4,384,209 | 5/1983 | Wagner et al. .................. 364/414 |
| 4,400,827 | 8/1983 | Spears .................. 378/159 |
| 4,544,949 | 10/1985 | Kurihara .................. 364/414 |

Primary Examiner—Joseph Ruggiero
Assistant Examiner—Kim Thanh Bui
Attorney, Agent, or Firm—Sandler & Greenblum

[57] ABSTRACT

A method of quantitatively determining the stenosis of the blood vessel using a digital subtraction angiographic image of the blood vessel. The method includes obtaining numbers proportional to the cross sectional areas of the blood vessel at stenosis portions and normal portions by obtaining density profiles less residual background from the images at those portions.

29 Claims, 7 Drawing Figures

— patent —

METHOD OF DETERMINING STENOSIS OF BLOOD VESSELS

FIELD OF THE INVENTION

This invention is concerned with methods of determining stenosis of blood vessels and more particularly with methods for using DSA (Digital Subtraction Angiography) equipment for determining stenosis of blood vessels with a reliable degree of accuracy.

BACKGROUND OF THE INVENTION

An advantage of DSA equipment is that it can be used for the evaluation of cardiovascular diseases. Doctors and clinicians have been attempting to use DSA equipment to aid in making quantitive measurements of stenosis (narrowing of the blood vessels) due to deposits on the vessel walls or, in a wider sense, any narrowing of the blood vessels. However, until now such measurements have not proven to be reliable. See for example, an article by Kruger R A, Anderson R E, Koshler R, Nelson J A, Sorenson J A, and Morgan T, entitled: "The Non-Invasive Evaluation of Cardiovasucular Dynamics Using a Radiographic Device", in Vol. 139, Radiology, pp 301 et seq. (1981). Another article of interest on the same subject is entitled: "Assessment of Quantatitive Indices of Arterial Stenosis Derived from Intravenous Digital Subtraction Angiography" by Peck W W, Slutsky R A, Brahme F, and Higgins C B. The article appeared in the American Heart Journal of Sept. 1984, pp 591 et seq.

The parameter which is usually used to quantify stenosis is the area ratio:

$$S=(An-As)/An$$

where An is the cross-sectional area at a "normal" location, and As is the cross-sectional area at a stenotic location.

Stenosis, as noted above, usually results from deposits (mostly fatty sometimes referred to as "scales") on the walls of the blood vessel. These deposits cause a narrowing of the aperture through which the blood flows, reducing the blood flow into the organ which is fed by the blood vessel. However, these deposits are very irregular: they occur in random locations along the vessel and where they do occur they appear in different angular positions. Thus, the cross-section of the blood vessel, which is circular when healthy without deposits on the walls (The circular shape is due to the combined action of the natural elasticity of the wall tissue and the pressure exerted by the blood.) becomes irregular.

In the subtracted image, numbers are assigned to pixels according to the amount of contrast medium (radiopaque dye) along the line of sight from the X-ray source to the portion of the image intensifier corresponding to the pixel. Those numbers are referred to for short and for historical reasons as "densities". For example, within the blood vessels the pixels have a high density value and outside the blood vessel the pixels have low density values. Thus, where the blood vessel passes over a portion of the pixel the assigned density number will be somewhere between the highest density level and the lowest density level. The pixels with no portion of a blood vessel thereon have the lowest density values. The pixels completely covered by a blood vessel have the highest density values. In actual fact, the amounts of contrast medium along the line of sight are proportional to the product of the opacity density of the contrast medium and the distance traversed by the X-ray line of sight within the contrast medium. However, the term "density" may be misleading as the opacity density may be assumed to be constant and where that assumption holds the amount of contrast medium is really proportional to the above distance. This distance is usually perpendicular to the plane of the image and therefore provides information about the third (unseen) dimension. The thicker the blood vessel the higher are the density values of the pixels covered by those blood vessels.

Existing methods for quantifying stenosis can be categorized as: geometric and densitometric. The geometric methods rely on measurements of the size of the blood vessel passageways in the X-ray image plane only. The densitometric methods rely in addition on the "density" data measurements (actually the thickness) of the blood vessel passageways and background in the X-ray images. Any measurement using only the location (x,y) of selected pixels are termed geometric, while, measurements using the additional density information in the pixels are termed densitometric.

All known geometric methods suffer from this irregularity of cross-section of the blood vessel described above as they use a small number of views (usually only one) of the vessel and assume a regular shape (circular for single views, elliptic for two views). Therefore, for example, if the cross-section of a stenotic blood vessel has an elongated shape then when the stenotic location is viewed so that the short side of the remaining passageway or opening of the blood vessel is towards the observer the geometric method will underestimate the cross-sectional area (sometimes grossly) and thus overestimate the stenosis. Conversely, if the long side is towards the observer the geometric method will tend to overestimate the cross-sectional area and sometimes overlook the stenosis completely.

Densitometric methods usually suffer from digitization errors and overlying (underlying) background. That is, there are too few pixels (pixels picture elements, derived from the digitization of the DSA image) across the blood vessel for a good fit to a mathematical function, and the background density (caused by underlying and overlying vessels which are below the resolution threshold, by scatter from other tissue etc;) makes direct integration inaccurate. In both cases quantum noise affects the results both by randomly modifying the values themselves and by randomly dithering the blood vessel edges, making it difficult to ascertain where to start measuring, integrating or fitting.

All presently existing methods for quantifying stenosis are deemed unusable by the clinicians, surgeons and diagnosticians. Repeating the measurement by two observers, and even by the same obeserver at a later time, gives widely differing quantitative results.

Although there are some who claim it is more important to measure the effect of the stenosis on the blood flow (the "significance" of the stenosis), it is generally considered important to be able to give a quantitative measure of the stenosis which is independent of the observer and relatively insensitive to the accuracy of the manual part of the operation.

A completely different problem is the definition of the above mentioned "normal" cross-section area. What is really needed is the cross-sectional area of the blood vessel without stenosis. This is an idealized quantity that can not be measured, and some approximation has to be chosen.

It may seem that an "atlas" of blood vessels may be compiled, giving the "normal" cross-section areas at each point (or at selected points). However, normal human variability combined with normal variations in imaging practice (size of image intensifier, distance of X-ray source and/or detector) make this impracticable. The scaling factor between the body and the image depends on the exact depth of the vessel within the body and only numbers proportional to the cross-sectional area can be derived.

Most existing methods use as an approximation to the "normal" cross-sectional area a measurement of the cross-sectional area at a nearby portion of the blood vessel which is considered by the physician to be "normal". This method suffers from drawbacks such as:

A. The selected portion may nevertheless be afflicted. It may be slightly stenotic, by an amount not discerned by the physician but which may affect the quantization of the stenosis. It may also be aneurismic (distended), due to an increase in blood pressure behind the impediment to free flow, also by an amount undiscerned by the physician but affecting the result. B. The normal shape of the blood vessels is tapering, starting with a very large diameter at the exit from the heart (the aortal) or at the entrance to it (the two vena cavae) and becoming progressively narrower as the distance from the heart increases. This narrowing is not at a constant rate but rather steplike or ramplike. Some stretches of vessel have a nearly constant diameter while others have relatively rapidly changing diameters. At the latter streches, using a different location to measure the "normal" cross-sectional area of the stenatic portion introduces an additional error.

Thus there is an ever present need for quantifying stenosis. More particularly there is a need for finding a method of quantifying stenosis that is relatively observer independent and capable of using measurements made by relatively unskilled technicians. The method should preferrably include a method of obtaining reliable and repeatable approximations of "normal" cross-sectional areas.

BRIEF DESCRIPTION OF THE INVENTION

Accordingly, a method is provided using DSA equipment for obtaining quantitative measurements of stenosis, said method comprising the steps of:

obtaining a DSA image (in density values or their complements) of vascular stenosis including normal vascular portions on both sides of the stenosis, drawing a first line on the image substantially perpendicular to the flow of blood in the location considered as having the maximum stenosis, segmentizing said first line into a plurality of equal segments, sequentially numbering the plurality of equal segments, which numbers represent locations along the said first line.

determining a density value for each of the segments, creating a density profile based on the density values versus the segment numbers, said profile having a maximum density value near the location of the center of the blood vessel, determining a background linear profile on said density profile according to the steps of:

selecting representative edge segments using the first segment from the center of the blood vessel in which a minimum occurs and segments further from the center of the blood vessel that said first segments, selecting representative density values of the edges using the said first minimum density values and the density values at said segments further from the center of the blood vessel than the first segments, creating said background linear profile through points determined by said representative density values and said representative edge segments, substracting values of the density profile from the background profile values for each of the segments to obtain second values, obtaining a new density profile from the second values, determining the total under the new profile between the representative edge segments, which total is proportional to the cross-sectional area of the blood vessel at the line, repeating said steps at a portion of the blood vessel considered to be without stenosis from drawing the first line to determine the total under the new profile, comparing the value determined at the portion of the blood vesel without stenosis with the value determined at the location considered to have the maximum stenosis to determine the percentage of stenosis.

According to a feature of the invention stenosis is quantitatively measured by:

creating a density profile of the blood vessel at a location of stenosis, removing the background from the density profile, integrating the density profile minus the background to obtain a value proportional to the cross-sectional area of the blood vessel at the location of stenosis, repeating the above steps at a normal location of the blood vessel to determine a value proportional to the cross-sectional area of the blood vessel at a normal location, and comparing the cross-sections at the location of stenosis and at the normal locations to obtain the percentage of stenosis in the blood vessel.

According to another feature of the present invention, the cross-sectional area of a normal portion of the blood vessel is determined by:

drawing lines at normal locations on both sides of the stenosis portion and determining the cross-sectional areas of the blood vessel at the lines at both sides of the stenosis area, averaging the cross-sectional areas, and using the average cross-sectional area as the normal area of the blood vessel to take care of the normal changes of cross-sectional area along the blood vessel due to tapering.

According to yet another feature of the invention, the method of determining the normal cross-sectional area of the blood vessel can be refined by using a plurality of lines at each side of the stenosis area.

BRIEF DESCRIPTION OF THE DRAWINGS

The above mentioned and other features and objects of this invention will be better understood when considered in the light of the following description of a broad aspect of the invention especially when taken in conjunction with the following drawings, wherein.

GENERAL DESCRIPTION

Figure 1A:
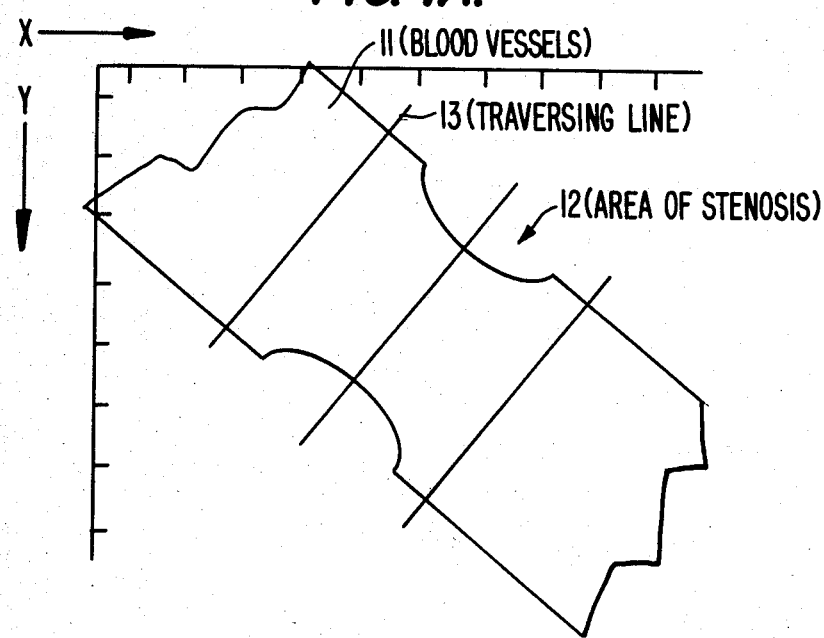
FIG. 1a, is an idealized line drawing showing a pixelized DSA image superimposed on a line drawing of a blood vessel.
Figure 1B:
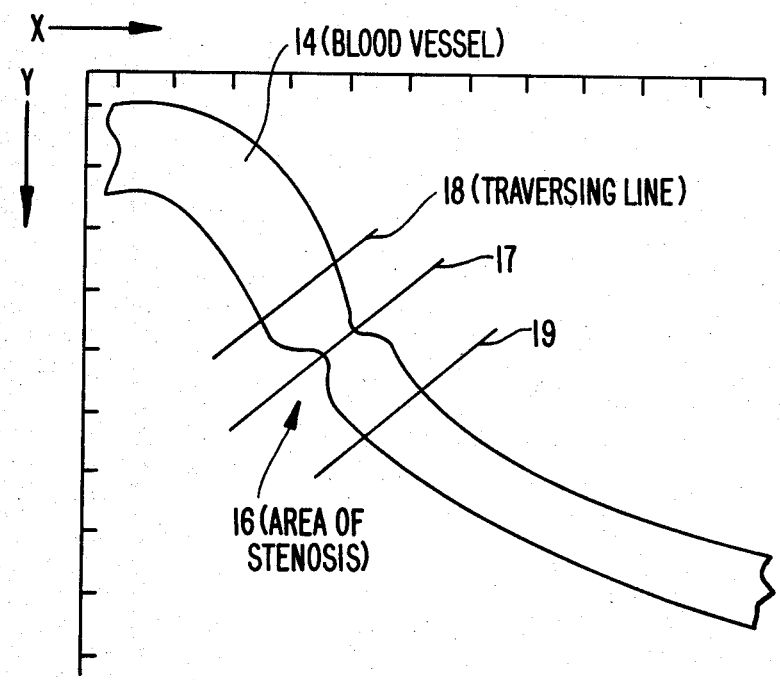
FIG. 1b is a similar showing of a pixelized image on DSA equipment of a blood vessel with the blood vessel depicted in a more natural meandering fashion.

FIG. 1a shows an idealized line drawing of a blood vessel superimposed on a line drawing of a pixelized DSA obtained image. The blood vessel is shown at 11 having a stenosis area 12 and also having tranversing lines such as line 13 traversing the blood vessel, and drawn substantially perpendicular to the flow of blood through the blood vessel 11. As is well known in DSA imaging, a dye is injected into the blood stream after a first image is taken. Generally speaking the first image and a subsequent image after the dye has passed through the blood vessel are substracted from one another so that all that ideally remains is the image of the dyed blood. Thus, the vascular system is emphasized in DSA imaging. However, until now there has been no reliable way of determining the percentage of blockage that has occurred in a blood vessel due to stenosis. FIG. 1b shows a blood vessel 14 which is a line drawing of a blood vessel that meanders in the manner of actual blood vessels. Blood vessels do not normally run in straight lines and remain the same size; instead the direction and size of the blood vessels normally vary.

In FIG. 1b an area of stenosis 16 is shown. A traversing line 17 is shown drawn through the center of the area of the stenosis, and further lines 18 and 19 are shown on both sides of the traversing line 17. The lines 18 and 19 are drawn through what appears to be normal portions of the blood vessel. The cross-sectional area of the blood vessel is determined at each of the lines, in the process of measuring the amount of stenosis in the blood vessel.

Figure 2:
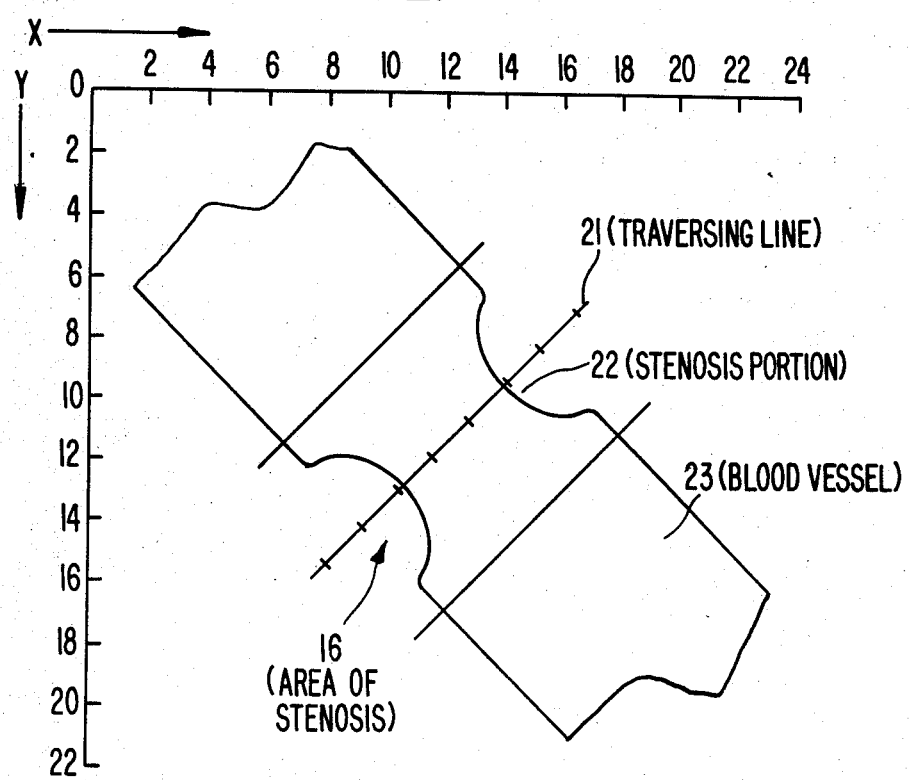
FIG. 2 is a line drawing showing a pixelized DSA image superimposed on a line drawing of a blood vessel shown by way of example, to illustrate how a blood density profile is determined.

FIG. 2 is used to demonstrate how to obtain a density profile along the traversing line. In FIG. 2 the pixels are shown as having location numbers; i.e. the pixels are each shown as having X and Y location numbers extending from 0-24 and 0-22, respectively. For example, a cursor is placed in the pixel which is substantially the center of the blood vessel at the point of maximum stenosis. From there the cursor is moved to a pixel on an imaginary straight line that is substantially perpendicular to the flow of blood through the blood vessel.

The traversing lines drawn through the blood vessel, are then segmentized into equal segments. A convenient measure with which to separate the points is the length of a pixel. For example, the line 21 in FIG. 2 on the stenosis portion 22 of the blood vessel 23 is broken into segments such as segments 24. Each of the segments is equal in length to the length of a pixel.

Each segment is assigned a sequential number. These sequential numbers are related to the location of the segment along the traversing line. In the above example the pixel selected as substantially the center of the blood vessel may be given the number "0". Alternatively the pixel at the end of the line may be given the number 1. (Both numbering systems are shown along the abscissa in FIG. 3).

Density values are assigned to the segments. Different ways may be used for assigning density values to the segments. For example, the value assigned to the segment can be that of the pixel in which the segment center is located or it can be the values of an imaginary new pixel drawn around the segment.

In a preferred embodiment of the invention the assigned value of the pixel whose center is closest to the center of the segments is used as the density value of that segment. If the center of the segment is equidistant between two pixel centers then the segment assumes the average value of the pixels.

Figure 3:
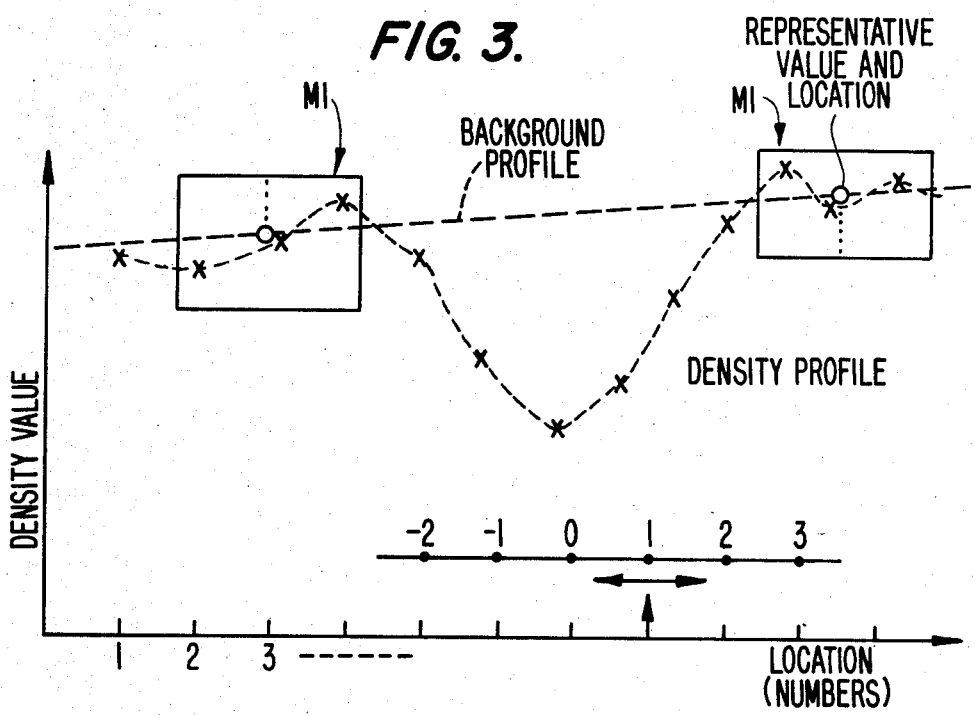
FIG. 3 is a graphical showing of the blood density profile.

Note that the curve of FIG. 3 goes from a maximum density value near the center point to a first local minimum density values at each side, where there could be more than one local minimum. The first local minimum determines the edges of the blood vessel and are marked by arrows in FIG. 3. The arrows of FIG. 3 mark the edges of the blood vessel. If there were no background in the X-ray picture such as the vestiges of other objects after substraction, then both minimum density values would be equal neglecting noise.

The edge locations may also be used for geometrically determining the cross sectional areas of the blood vessel within the scope of this invention.

However, in real life, there is background and noise. The preferred method of the invention enables compensating for the background even in the presense of noise using the background line determination.

More particularly, moving along the traversing line away from the maximum density point, a first minimum density point is reached shortly after the traversing line passes beyond the blood vessel on each side. The density values of each minimum segment and a few segments after these mimima are averaged in a preferred embodiment to provide a density value representative of the edge density value of the blood vessel on each side. The average density is less affected by quantum noise that the unaveraged minimum density value.

Other approaches to the noise problem in the past addressed the difficulty in finding the minimum. These approaches include: (a) smoothing the profile until only a single maximum exists; (b) using a threshold so that the difference between the maximum value and the minimum value must exceed the threshold; and (c) using the lowest minimum. Each of the approaches has its own advantages and its own disadvantages.

A representative location for the edge of the blood vessel is also selected. For example, the locations of the segments at the first minimum or at the minimal minimum can be used. An average of the locations of the segments used to determine the representative average value can also be used. The points defined by the representative density values and locations of the edges of the blood vessel are now connected by a straight line, hereinafter referred to as the "background line". The background line is shown in FIG. 3 in dashed line form.

Figure 4:
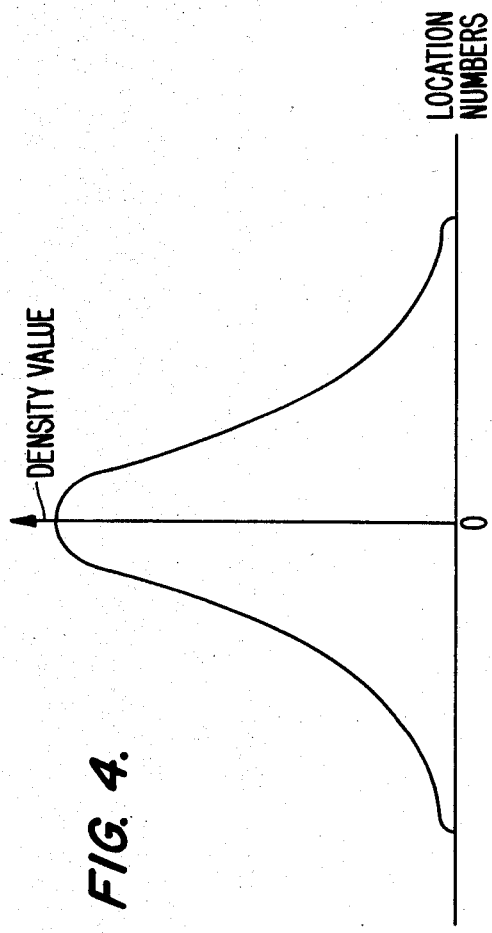
FIG. 4 is a graphical showing of the DSA image background minus the blood density profile values of FIG. 3.

After the blood density profile and the background line are obtained, the values of the blood density profile is subtracted from the values of the background line. That is, the values of the background line at each segment is subtracted from the values of the blood density profile to provide a profile of the background values minus the density values. This curve is shown in FIG. 4. Note that the value beyond the intersection of the background line and the blood density profile are treated as zero.

The area under the curve of FIG. 4 is a number that is proportional to the cross-sectional area of blood vessel at the plane perpendicular to the blood flow that includes the traversing line. Thus, the area under the curve of FIG. 4 provides a numerical value that is proportional to the open cross-sectional area of the blood vessel at the location of maximum stenosis as selected by line 21 of FIG. 2.

To obtain the stenosis ratio or the percentage of the stenosis it is necessary to also determine the cross-sectional area of the blood vessel at a normal location, i.e. without stenosis. This is done in a preferred embodiment by repeating at a normal portion of the blood vessel the steps of:

drawing the traversing line perpendicular to the flow of blood, segmentizing the traversing line into segments of equal size, assigning sequential numbers to the segments whereby the sequential numbers are related to the locations of the segments, assigning density value to the segments, creating a first density profile, determining the edges of the blood vessel, assigning representative segment numbers to the edges, assigning representative density values to the edges of the blood vessel, said representative segment numbers and density values defining points representing opposite edges of the blood vessel.

subtracting the background line density values from the density values of the first density profile, creating a new background minus density value profile from the values obtained, and determining the area under the new profile which is a number proportional to the cross-sectional area of the blood vessel at a plane including the traversing line and perpendicular to the blood flow in the selected normal portion of the blood vessel being analysed.

The steps may be repeated again for a third traversing line (or more); preferably on the other side of the stenosis. Numbers proportional to the cross-sectional area of the normal blood vessel are obtained at the second and third traversing lines. The difference between the numbers proportional to the cross-sectional area at a normal portion of the blood vessel and the cross-sectional area at the stenosis is divided by the number proportional to the cross-sectional area of the normal portion of the blood vessel to provide a reliable stenosis ratio.

Usually, two outer traversing lines are used because, for example, the blood vessel may be decreasing in size in a normal manner. If only one traversing line is used in addition to the traversing line placed at what appears to be a stenosis and the one line is on the side of blood vessel that is normally larger than the blood vessel the stenotic portion than what is actually a minor diminution in cross-sectional area could appear as a serious stenosis. If the second traversing line, on the other hand, were on the side of the apparent stenosis where the blood vessel is naturally smaller in cross-sectional area, then a serious stenosis could be analysed as minor. By using a traversing line on each side of what appears to be a stenosis, a more reliable diagnosis of the stenosis is obtained. This can be further improved of course by using more traversing lines at normal locations on each side of the area of apparent stenosis.

Figure 5:
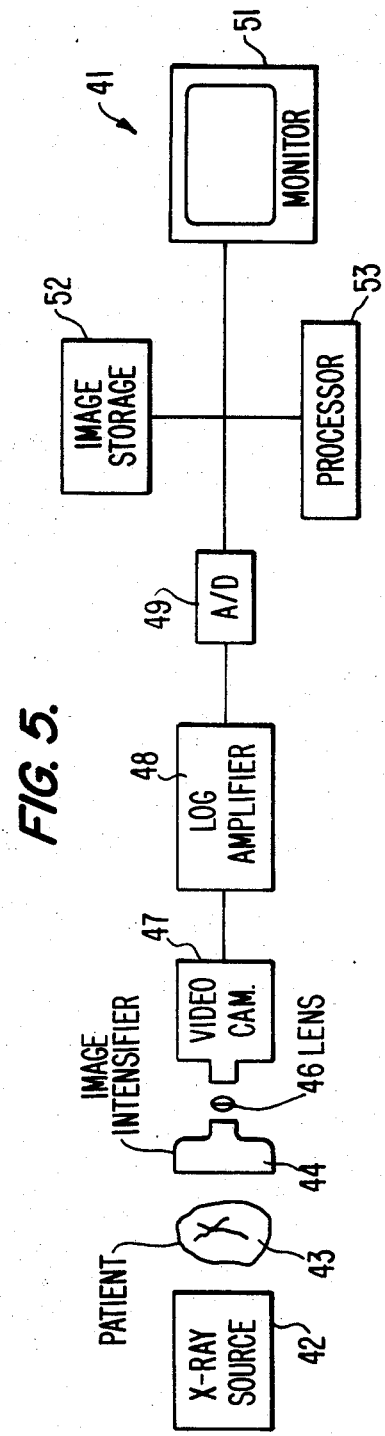
FIG. 5 is a block diagram of a DSA system for obtaining images whose pixel values are linearly dependent on the densities.

The digital fluorography system 41 of FIG. 5 is an example of a system that can be used to determine the stenosis of blood vessels. The system comprises an X-ray source 42 which directs penetrating radiation through a patient 43. The radiation which passes through the patient is detected by the image intensifier 44. The image of the intensifier is directed by optical means 46 to a video camera 47 which electronically scans the image. The location related analog output of the camera is amplified by log amplifier means 48 to provide a signal that is a function of a constant minus the density of the body parts in the path of the radiation. Without the log amplifier the analog signal is an exponential function i.e. $e-(c-d)$; where c is a constant and d is density of objects in the x-ray path.

The location related analog output is changed to a location related digital signal in the analog to digital convertor 49. The digital signal provides the data for the image on the monitor 51. A storage means 52 is provided for use in the system. The system is controlled by processor 53.

Figure 6:
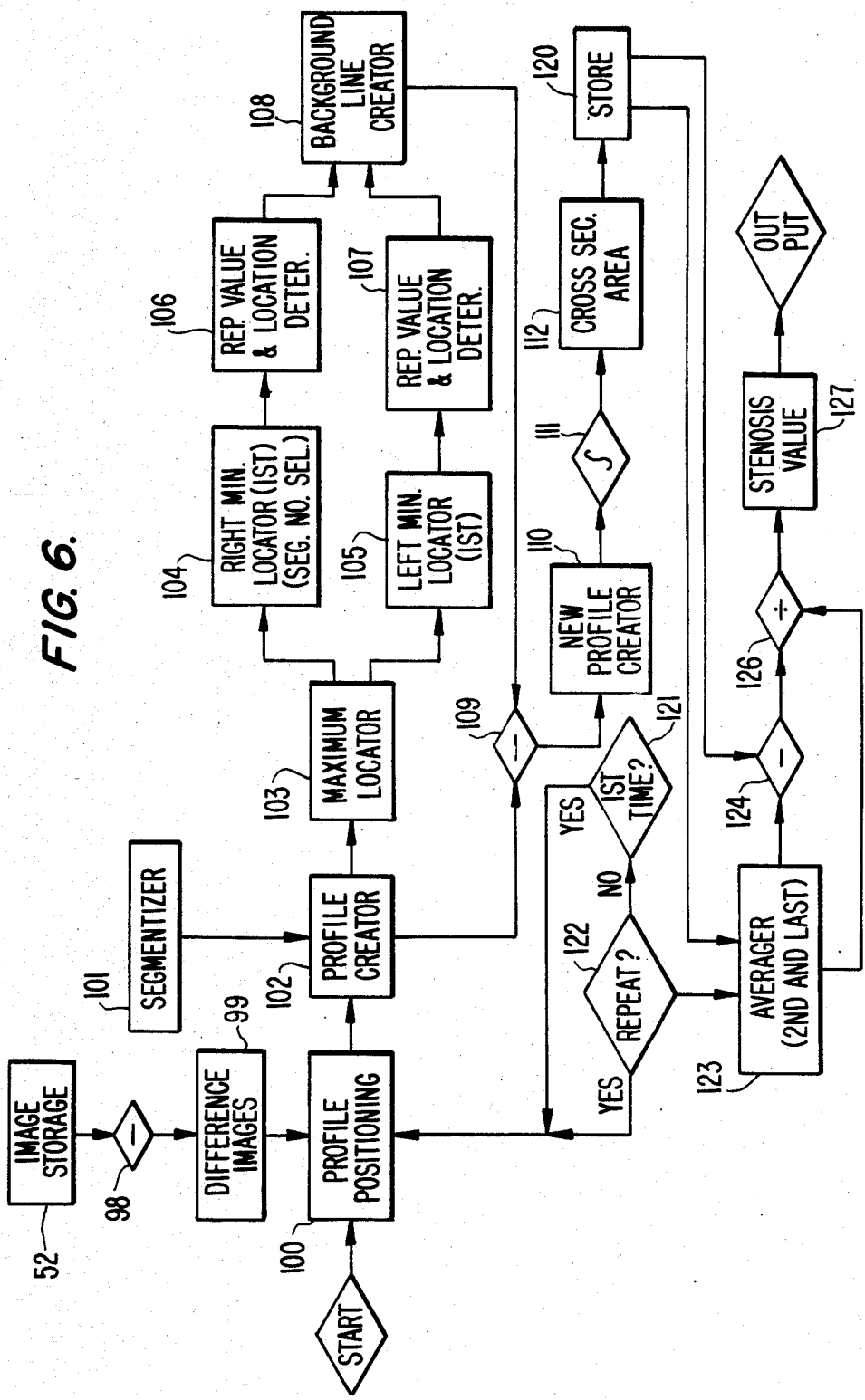
FIG. 6 is a block diagram of the stenosis determining system.

Functions of the processor are illustrated in the block diagram of FIG. 6. The image storage means 52 provides density values for images before and after contrast material is administered to the patient. The images are subtracted as indicated by block 98. The difference images of block 99 are used for the quantitative stenosis measurement of the invention.

As a start for the stenosis determination a first traversing line is positioned at the point of maximum apparent stenosis as indicated at unit 100. A first density profile is created by unit 102 in conjunction with the segment sizer 101 which divides the line of unit 100 into segments. In this manner a density profile of the stenosis area is obtained.

Means are provided for obtaining the background lines. More particularly, at least one maximum is located as illustrated at unit 103. As FIG. 6 indicates a right and left minimum density value are located by units 104 and 105. The representative segment location numbers and density values for the minimum points are then assigned by averaging the density values and segment numbers of segments beyond the segments having minimum density values as indicated at units 106 and 107. The assignments provide two points detining the background line indicated at unit 108.

The profile of 102 is subtracted from the background line of 108, as illustrated at 109 to provide the new profile of 110. The area under the new profile is determined by integrator 111 as a number proportional to the cross sectional area 112 at the stenosis afflicted portion of the blood vessel. That number is stored at 120.

The system then repeats the operation to determine the number proportional to the cross sectional area of a normal portion of the blood vessel. This is accomplished by repeating the traversing line positioning and the forming of a density profile at a location on at least one normal portion of the blood vessel and preferably at two normal portions of the blood vessel, one on either side of the stenosis.

In FIG. 6 this repetition of steps indicated by determining at 121 if the cross sectional area determination of unit 112 is a first determination. If so, the line positioning and further operations are repeated as indicated at 122. More particularly, if the cross-sectional area value of 112 is a first determination then a decision is made at 122 to place a new traversing line at the normal portion of the blood vessel on the other side of the stenosis).

When the decision is not to repeat, then, the proportional cross sectional area values in the store 120, except the first value, are averaged at 123. The first value is subtracted from the averaged (normal) value at 124. The difference is divided by the normal value at 126 to give the stenosis ratio value at 127.

In practice the percentage of stenosis is arrived at by obtaining a DSA image of the blood vessel. A first traversing line is then located on the image of the blood vessel at an apparent or suspected area of stenosis. The line is segmentized into equal segments. The segments are provided with location defining numbers. Density values are assigned to the segments based on the density signal values of the image at the segments. In the sample drawing of FIG. 3 a blood density profile is drawn by plotting a constant minus density versus position. The background of the blood vessel density profile is determined. A subtraction process is used to eliminate the background and a new profile curve is drawn that is the density profile without the background. The new curve is integrated to obtain the area under the curve in the form of a number that is proportional to the cross sectional area of the blood vessel. These steps are repeated at least at an area of the blood vessel that appears normal to obtain a ratio between the cross sectional area at the stenosis and at what appears to be a normal portion of the blood vessel. More line can be used to refine the process.

While the invention is explained using exemplary embodiments, it should be understood that these embodiments are used by way of example only and not as a limitation on the scope of the invention.

What is claimed is:

1. A method for using digital subtraction angiography (DSA) equipment to obtain quantitative measurements of stenosis, said method comprising the steps of:
   obtaining a DSA pixelized image of a blood vessel including a stenotic portion and a normal portion of the blood vessel;
   determining a number proportional to the cross sectional area of the blood flowing through the blood vessel at said stenotic portion of the blood vessel;
   determining a number proportional to the cross sectional area of the blood flowing through the blood vessel at said normal portion of the blood vessel;
   said steps of determining a number proportional to the cross section area of the blood flowing comprising the steps of:
   creating density profiles across the blood vessel at said stenotic portion and at said normal portion;
   detecting the edges of the blood vessel on the density profiles;
   evaluating residual density background values along the density profiles;
   compensating total density values for said residual density background values to obtain compensated total density values which are numbers proportional to the cross sectional area of the blood flowing through the blood vessel at the normal portion and at the stenotic portion; and
   using the compensated total density values at the normal portion and at the stenotic portion of the blood vessel to quantitatively determine stenosis.

2. The method of claim 1 wherein the step of using the compensated total density values along each of the profiles comprises the step of:
   using said compensated total density values for determining a stenosis ratio.

3. The method of claim 2 wherein said stenosis ratio is determined by using the steps of:
   subtracting said compensated total density values for the stenotic portion from said compensated total density values for said normal portion, and dividing the difference by said compensated total density values for said normal portion.

4. The method of claim 1 wherein said step of creating one of said density profiles comprises the steps of:
   determining a traversing line substantially perpendicular to the flow of blood at a selected portion of the blood vessel,
   segmentizing said traversing line into segments of equal lengths,
   assigning sequential segment numbers to said segments which numbers represent locations along said traversing line,
   assigning density levels to the segments based on the density values of the pixels traversed by the segments in the pixelized image, and
   using the assigned segment numbers and density levels to provide a blood density profile of the blood vessel at the said traversing line.

5. The method of claim 4 wherein the step of determining a number proportional to the cross sectional area at said normal portion comprises using a plurality of traversing lines which are all substantially perpendicular to blood flow at portions of the image where the blood vessel is considered normal.

6. The method of claim 5 wherein one of said plurality of traversing lines is drawn through said stenotic portion, a second of said plurality of traversing lines is drawn through said normal portion on one side of said stenotic portion and a third of said plurality of traversing lines is drawn through a normal portion on the other side of said stenotic portion, and wherein the numbers proportional to the cross sectional areas at said second and third traversing lines are averaged to provide said number proportional to the cross sectional area of the blood flow at said normal portion of the blood vessel.

7. The method of claim 4 wherein the step of detecting the edges of the blood vessel include the step of:
   selecting as edge locations first segments located at a first minimum density value on each side of the location of a maximum density value.

8. The method of claim 4 wherein the step of detecting the edges of the blood vessel includes the step of:
   selecting as edge locations the segments at the minimal minimum density value on each side of the location of maximum density value.

9. The method of claim 7 or 8 wherein the profile is first smoothed to have only one location of the maximum density.

10. The method of claim 7 wherein a threshold is used allowing only minimum density values that are below the said threshold.

11. The method of claim 7 of 8 wherein the step of evaluating the residual density background comprises the steps of:
    selecting segments of the said traversing line which are further from the locations of the maximum density than the edge locations at each side, and fitting a function to the density value at said selected segments and said edge locations which function represents the background of the blood density profile.

12. The method of claim 11 wherein said function is a linear function.

13. The method of claim 11 wherein said fitting comprises using a least squares fit.

14. The method of claim 7 or 8 including the steps of: finding representative density values by using the density values at each of the edge locations and the values of the density at segments that are further from the location of the maximum density than each of the edge locations, and finding representative locations by using the segment numbers of each of the edge location segments and said segments further than each of the edge location segments.

15. The method of claim 14 and the step of: using said representative locations and representative density values on each side of said maximum density value to evaluate the residual density background along the profile, and wherein the step of evaluating the residual density background along the profile comprises using said representative locations and representative density values to determine a linear function which represents the background of the blood density profile.

16. The method of claim 15 wherein the linear function yields the representative density values at the corresponding representative locations.

17. The method of claim 15 including the step of: assigning a background value to each segment of the traversing line, said background value being based on the values yielded by the said linear function at said segment.

18. The method of claim 17 wherein the step of compensating said density profile includes the step of: obtaining differences by subtracting the residual background density value assigned to each segment of the traversing line from the representative density value assigned to the corresponding segment.

19. The method of claim 18 wherein the segments further from the location of the maximum density value than the edge compensated are assigned the value zero.

20. The method of claim 18 wherein the step of finding the total compensated density along the profile comprises the step of summing the differences.

21. The method of claim 20 wherein the summing the differences consists of summing between the edge locations.

22. The method of claim 17 wherein the step of compensating said total density for said residual background comprises the steps of:
finding the total background between the edges, and subtracting said total background from said total density.

23. The method of claim 21 wherein the step of finding the total background comprises:
summing the background values assigned to the segments of the traversing line between the edge locations.

24. The method of claim 22 wherein the step of finding the total background comprises integrating analytically the said linear function between the edge locations.

25. The method of claim 14 wherein said segments further from the maximum density value than said edge locations consist of the segments sequentially contiguous to the edge locations.

26. The method of claim 14 wherein the step of finding the representative values includes a step of reducing the effects of noise.

27. The method of claim 26 wherein the step of reducing the effects of noise comprises averaging the density values at the edge locations and at said segments which are further that the edge locations from the location of the maximum density and on the same side of the maximum density as said edge locations.

28. A method for using digital subtraction angiography (DSA) equipment to obtain quantitative measurements of stenosis, said method comprising the steps of:
obtaining a DSA pixelized image of blood vessel including a stenotic portion and a normal portion of the blood vessel,
determining a number proportional to the cross sectional area of the blood flowing through the blood vessel at said stenotic portion of the blood vessel,
determining a number proportional to the cross sectional area of the blood flowing through the blood vessel at said normal portion of the blood vessel;
said step of determining a number proportional to the cross sectional area of the blood flowing comprises the steps of:
creating a density profile across the blood vessel,
detecting the edges of the blood vessel on the profile,
using the distance between the edges to obtain the numbers proportional to the cross sectional areas of the blood vessel; and using the said numbers to quantitatively determine stenosis.

29. The method of claim 28 wherein the step of using the distance comprises multiplying the distance squared by a constant.

* * * * *